(12) United States Patent
Constantine et al.

(10) Patent No.: US 9,457,203 B2
(45) Date of Patent: Oct. 4, 2016

(54) EXFOLIATING COMPOSITION BASED ON CREAM OF TARTAR AND BICARBONATE

(75) Inventors: Mark Constantine, Poole (GB); Margaret Joan Contantine, Poole (GB); Rowena Jacqueline Bird, Bournemouth (GB); Helen Elizabeth Ambrosen, Wimborne (GB)

(73) Assignee: Cosmetic Warriors Limited, Poole, Dorset (GB)

( * ) Notice: Subject to any disclaimer, the term of this patent is extended or adjusted under 35 U.S.C. 154(b) by 0 days.

(21) Appl. No.: 13/122,943

(22) PCT Filed: Oct. 5, 2009

(86) PCT No.: PCT/GB2009/051306
§ 371 (c)(1),
(2), (4) Date: Oct. 25, 2011

(87) PCT Pub. No.: WO2010/041050
PCT Pub. Date: Apr. 15, 2010

(65) Prior Publication Data
US 2012/0040919 A1   Feb. 16, 2012

(30) Foreign Application Priority Data
Oct. 7, 2008   (GB) .................................. 0818336.0

(51) Int. Cl.
| | | |
|---|---|---|
| A61K 8/60 | (2006.01) | |
| A61K 8/67 | (2006.01) | |
| A61K 8/92 | (2006.01) | |
| A61Q 19/00 | (2006.01) | |
| A61Q 19/10 | (2006.01) | |
| A61K 8/19 | (2006.01) | |
| A61K 8/365 | (2006.01) | |

(52) U.S. Cl.
CPC ................. *A61Q 19/00* (2013.01); *A61K 8/19* (2013.01); *A61K 8/365* (2013.01); *A61K 8/60* (2013.01); *A61Q 19/008* (2013.01); *A61Q 19/10* (2013.01); *A61K 2800/28* (2013.01)

(58) Field of Classification Search
None
See application file for complete search history.

(56) References Cited

U.S. PATENT DOCUMENTS

| 5,523,017 | A  | * | 6/1996  | Moran et al. ................. 510/447 |
|---|---|---|---|---|
| 6,015,242 | A  |   | 1/2000  | Gillis |
| 6,177,092 | B1 |   | 1/2001  | Lentini et al. |
| 6,696,396 | B1 |   | 2/2004  | Arneson |
| 2003/0219464 | A1 | * | 11/2003 | Incando et al. ............... 424/401 |
| 2005/0123573 | A1 | * | 6/2005  | Spadini et al. ............... 424/401 |

FOREIGN PATENT DOCUMENTS

| EP | 0363569 A1 | * | 4/1990 |
|---|---|---|---|
| EP | 0363569 A1 | * | 4/1990 |
| GB | 955 111 |  | 4/1964 |
| GB | 1005161 |  | 9/1965 |
| GB | 2 346 619 |  | 8/2000 |
| GB | 2346557 A |  | 8/2000 |
| GB | 2346619 A | * | 8/2000 |
| WO | WO 96/10987 |  | 4/1996 |
| WO | WO0101954 A1 | * | 1/2001 |
| WO | WO03037287 A1 | * | 5/2003 |
| WO | WO 2008/023145 |  | 2/2008 |
| WO | WO 2008023145 A1 | * | 2/2008 |
| WO | WO 2008034180 A1 | * | 3/2008 |
| WO | WO 2008/047148 |  | 4/2008 |
| WO | WO 2008043163 A1 | * | 4/2008 |
| WO | 2008056997 A2 |  | 5/2008 |

OTHER PUBLICATIONS

Remington, "The Science and Practice of Pharmacy," Part 5, Pharmaceutical Manufacturing, (1889) pp. 1088.

* cited by examiner

*Primary Examiner* — Bethany Barham
*Assistant Examiner* — Dominic Lazaro
(74) *Attorney, Agent, or Firm* — Merchant & Gould P.C.

(57) ABSTRACT

A solid exfoliating composition includes a surfactant, sodium bicarbonate, cream of tartar, and a granular exfoliant.

15 Claims, No Drawings

EXFOLIATING COMPOSITION BASED ON CREAM OF TARTAR AND BICARBONATE

This application is a National Stage Application of PCT/GB2009/051306, filed 5 Oct. 2009, which claims benefit of Ser. No. 0818336.0, filed 7 Oct. 2008 in Great Britain and which applications are incorporated herein by reference. To the extent appropriate, a claim of priority is made to each of the above disclosed applications.

FIELD OF THE INVENTION

The present invention relates to a solid exfoliating composition, a process for producing said solid exfoliating composition, and a cosmetic method for using the solid exfoliating composition.

BACKGROUND TO THE INVENTION

Exfoliation of the skin can be undertaken by either chemical or mechanical means. Chemical exfoliation involves the process of applying to the skin a chemical which strips away the top layer of the skin.

By contrast, mechanical exfoliation involves the removal of dead skin using coarse or granular materials. Such coarse materials may include pumice stones and the like.

Granular mechanical exfoliants are typically known in the art as body scrubs. Body scrubs and the like are commonly used in cosmetic applications to remove layers of dead skin from the user. Their use results in the improvement of the appearance of the skin of the user, as well as rendering the skin smoother. Facial scrubs, foot scrubs etc. may fall within the general meaning of the term body scrub depending on the area of the body to which they are applied. Although such scrubs may be individually formulated to suit the particular application, e.g. a facial scrub may have finer granules than a foot scrub, they all fall within the broad classification of a body scrub.

The term "user" includes an individual who applies an exfoliating composition to the body of another individual, as well as an individual who has an exfoliating composition applied to their body by another individual. It also includes an individual who applies an exfoliating composition to their own body.

The body scrubs of the prior art are in a liquid or paste like form. They are contained in appropriate packaging which allows the user to apply the body scrub to the desired parts of the body. For example, WO 08/047,148 and WO 08/023,145 disclose exfoliant body scrubs of a fluid or paste like composition.

However, the required use of packaging is a disadvantage to the body scrubs of the prior art. From an environmental perspective, waste packaging is a significant problem, despite the availability of recycling.

The present invention seeks to provide an exfoliating composition which does not require packaging, yet remains in a usable state when stored.

SUMMARY OF THE INVENTION

In a first aspect, there is provided a solid exfoliating composition comprising a surfactant, sodium bicarbonate, cream of tartar, and a granular exfoliant.

In a second aspect, there is provided a process for the production of a solid exfoliating composition comprising the steps of:

i) preparing a mixture comprising a surfactant, sodium bicarbonate and cream of tartar;
ii) combining a granular exfoliant with the mixture of step i); and,
iii) allowing the mixture of step ii) to solidify.

In a third aspect, there is provided a cosmetic method of exfoliating the skin comprising massaging the moist skin of a user with the solid exfoliating composition of the present invention.

For ease of reference, these and further aspects of the present invention are now discussed under appropriate section headings. However, the teachings under each section are not necessarily limited to each particular section.

ADVANTAGES

The solid exfoliating composition of the present invention does not require additional packaging. Thus, the solid exfoliating composition of the present invention can be stored and applied directly to the skin of a user, without additional packaging. As a result, the environmental impact of waste packaging is greatly reduced.

The solid nature of the exfoliating composition is further advantageous for users who are travelling with the product. Not only is the weight and volume of the product reduced, in scenarios where volume of liquid carried is restricted, such as during airline flights, the present product allows for the user to still carry the product The solid exfoliating composition of the present invention also provides an exfoliating composition which not only exfoliates (removes dead skin), but also removes excess dirt and grease from the skin. This is achieved through the use of a solid exfoliating composition comprising both a granular exfoliant and a surfactant.

The solid exfoliating composition of the present invention may also provide an exfoliating composition in which the granular exfoliant is evenly distributed. Body scrubs of the prior art are presented in paste or liquid form, and thus can result in the sedimentation of the granular material. Such sedimentation can lead to inefficient application of the scrub to the user's skin, as well as leading to dispensing issues resulting from clogged packaging etc. Due to the solid form of the exfoliating composition of the present invention, these problems associated with sedimentation are overcome.

DETAILED DESCRIPTION

Composition

As discussed herein, in one aspect of the present invention, there is provided a solid exfoliating composition comprising a surfactant, sodium bicarbonate, cream of tartar, and a granular exfoliant.

Solid exfoliating compositions of the present invention include those compositions which can substantially sustain their physical shape when unsupported by external means, e.g. packaging etc. Thus, they are considered to be solid, solid like, in solid form or in solid-like form at room temperature.

By solid-like, it is understood that some materials are considered on a day to day basis to be solid, yet over an extremely long period of time, may alter in shape, e.g. amorphous materials such as glass etc. However, they are considered to be solid-like as, for the purpose they fulfil, they are solid.

As mentioned above, due to the solid form of the exfoliating compositions of the present invention, external packaging is not required to maintain the shape of the composition.

The solid exfoliating composition of the present invention comprises a surfactant. The surfactant is primarily selected from those surfactants known in the art to be suitable for application to the skin. In one embodiment, the surfactant is selected from the group consisting of sodium laureth sulfate, cocamide diethanolamine, lauryl betaine and mixtures thereof.

In one embodiment, the surfactant is a mixture of sodium laureth sulfate, cocamide diethanolamine and lauryl betaine.

In one embodiment, the surfactant is present in an amount of from about 1% to about 10% by weight of the total composition. Thus, where one surfactant is present, it may be present in an amount of from about 1% to about 10% by weight of the total composition. In a similar manner, where the surfactant is a mixture of one or more surfactants, the total amount of surfactant present is from about 1% to about 10% by weight of the total composition.

In one embodiment, the surfactant, or the mixture of surfactants, is present in an amount of from about 2% to about 8% by weight of the total composition.

In one embodiment, the surfactant, or the mixture of surfactants, is present in an amount of from about 4.5% to about 7% by weight of the total composition.

In one embodiment, the surfactant, or the mixture of surfactants, is present in an amount of about 6.5% by weight of the total composition.

The surfactant of the solid exfoliating composition provides the composition with the ability to remove dirt and grease from the user's skin, in addition to the ability to exfoliate. The incorporation of the surfactant onto the user's skin results in the production of a desirable lather or foam when the solid exfoliating composition is massaged against the moist skin of a user.

The solid exfoliating composition of the present invention also comprises sodium bicarbonate. In one embodiment, sodium bicarbonate is present in an amount of from about 9% to about 18% by weight of the total composition.

In one embodiment, sodium bicarbonate is present in an amount of from about 10% to about 15% by weight of the total composition.

In one embodiment, sodium bicarbonate is present in an amount of about 12% by weight of the total composition.

The solid exfoliating composition of the present invention also comprises cream of tartar. Cream of tartar is also known as potassium bitartrate or potassium hydrogen tartrate. It is the mono-potassium salt of 2,3-dihydroxybutanedioic acid. Thus, the cream of tartar used in the solid exfoliating composition of the present invention encompasses any product which is considered to be cream of tartar by virtue of it substantially comprising potassium hydrogen tartrate.

In one embodiment, the cream of tartar of the solid exfoliating composition is potassium hydrogen tartrate.

In one embodiment, the cream of tartar is present in an amount of from about 4.5% to about 9% by weight of the total composition.

In one embodiment, the cream of tartar is present in an amount of from about 5% to about 7% by weight of the total composition.

In one embodiment, the cream of tartar is present in an amount of about 6% by weight of the total composition.

The combination of sodium bicarbonate and cream of tartar in the solid exfoliating composition of the present invention is critical to the ability of the composition to effectively hold the granular exfoliant in suspension throughout the solid.

The solid exfoliating composition of the present invention also comprises a granular exfoliant. A granular exfoliant includes any material which is in granular form, and of sufficient coarseness to effect the removal of dead skin from the user on application. The granular exfoliant present in the solid exfoliating composition may be of a single type or may be a mixture of one or more different types.

The granular exfoliant includes any material in granular form which is considered to be cosmetically acceptable for skin applications.

In one embodiment, the granular exfoliant is selected from the group consisting of cosmetically acceptable sugar, salt, seeds, sand, clay, ground nuts, ground shell, pumice and mixtures thereof.

Where ground nuts are used as a granular exfoliant, any type of ground nut may be used. In one embodiment, the ground nut is ground almond.

In a similar manner, ground shell includes the ground shell of nuts. In one embodiment, the ground shell is ground almond shell. The ground shell may also include the ground shell of abandoned seashells.

In one embodiment, the granular exfoliant is cosmetic grade caster sugar.

In one embodiment, the granular exfoliant is present in an amount of from about 50% to about 85% by weight of the total composition.

In one embodiment, the granular exfoliant is present in an amount of from about 55% to about 80% by weight of the total composition.

In one embodiment, the granular exfoliant is present in an amount of about 75% by weight of the total composition.

The solid exfoliating composition of the present invention may also comprise one or more cosmetically acceptable additives. The person skilled in the art is aware of a range of cosmetically acceptable additives which are suitable for incorporation into such compositions. Fruit and herb extracts and juices, vegetable oils and essential oils are all compatible with the composition. Colours, both naturally derived and synthetic can be used to colour the solid exfoliating composition.

In one embodiment, the cosmetically acceptable additives are selected from the group consisting of essential oils, vitamins, fragrances, colourings, decorative articles and mixtures thereof.

In one embodiment, the cosmetically acceptable additives are present in amount of from about 0.2% to about 3% by weight of the total composition.

The essential oils will be selected based on the fragrance desired, skin type to be treated and other effects desired based on the well known properties of essential oils. The addition of essential oils, when taken in to the nose, are known to alter mood. For example, essential oils are known to create effects of drowsiness or stimulating the senses. Many well documented effects can be achieved by the use of essential oils.

In one embodiment, the one or more essential oils present in the solid exfoliating composition are selected from tea tree oil and lavender oil. Other essential oils may be present such as rose oil.

As discussed herein, vitamins, particularly B, C and E are very beneficial for the skin. Vitamin rich ingredients such as Wheatgerm oil can also be used to deliver vitamins on to the skin. In a one embodiment, the vitamins are selected from vitamin B, vitamin C, vitamin E and mixtures thereof. It will be appreciated by one skilled in the art that the vitamin may be provided from any suitable source. For example the vitamin(s) may be provided from a synthetic source or from incorporation into the solid exfoliating composition of a material, such as a natural material, that has a high vitamin content.

The ingredients in the present invention do not require cosmetic preservatives, solublisers or alcohols, such as ethanol. The use of cosmetic preservatives can increase the potential to irritate the skin. The use of alcohols can cause the skin to become dry. Equally, fragrances do not need to be solublised and therefore solublisers can be avoided.

The decorative items which may be present in the solid exfoliating composition include items such as glitter and sequins etc.

In a preferred embodiment, the solid exfoliating composition comprises a surfactant in an amount of from about 1% to about 10%, sodium bicarbonate in an amount of from about 9% to about 18%, cream of tartar in an amount of from about 4.5% to about 9%, and a granular exfoliant in an amount of from about 50% to about 85% by weight of the total composition.

In a preferred embodiment, the solid exfoliating composition comprises a surfactant in an amount of from about 2% to about 8%, sodium bicarbonate in an amount of from about 10% to about 15%, cream of tartar in an amount of from about 5% to about 7%, and a granular exfoliant in an amount of from about 55% to about 80% by weight of the total composition.

In a preferred embodiment, the solid exfoliating composition comprises a surfactant in an amount of about 6.5%, sodium bicarbonate in an amount of about 12%, cream of tartar in an amount of about 6%, and a granular exfoliant in an amount of about 75% by weight of the total composition.

The above ranges provide preferred amounts of each of the components. Each of these ranges may be taken alone or combined with one or more other component ranges to provide a preferred aspect of the invention.

Process

In another aspect, there is provided process for the production of a solid exfoliating composition comprising the steps of:
i) preparing a mixture comprising a surfactant, sodium bicarbonate and cream of tartar;
ii) combining a granular exfoliant with the mixture of step i); and,
iii) allowing the mixture of step ii) to solidify.

The shape of the solid exfoliating compositions of the present invention is not limited. It may be that the solid exfoliating compositions are provided with a shape which would be aesthetically pleasing and/or which aids in the application of the composition to the skin. For example, it may be that the solid exfoliating composition is produced in such a manner so that it solidifies in a shape which is ergonomically acceptable to the user.

Therefore, in one embodiment of the process of the present invention, the mixture of step ii) is caused to solidify in a predetermined shape.

In one embodiment of the process of the present invention, the mixture of step ii) is pressed into a mould, allowed to solidify, and then turned out to produce the solid exfoliating composition.

As described herein, the solid exfoliating composition may further comprise one or more cosmetically acceptable additives. In one embodiment, the process further comprises the step of combining with the mixture of step i) or step ii) one or more cosmetically acceptable additives as defined above, Method In one aspect of the present invention, there is provided a cosmetic method of exfoliating the skin comprising massaging the moist skin of a user with the solid exfoliating composition as defined herein.

The cosmetic method of the present invention can be applied to various areas of the skin, including the face, feet, torso or any other part of the body which may require cosmetic exfoliation.

As described herein, the moist skin of a user is massaged with the solid exfoliating composition of the present invention. Once the desired effect has been achieved, any excess of the composition can be removed by rinsing the applied area with water.

EXAMPLES

The invention will now be described with reference to the following non-limiting example.

A solid exfoliating composition having the following composition was prepared.

The formula is as follows:

|  | Wt % |
| --- | --- |
| Sodium bicarbonate | 12.0 |
| Sodium laureth sulfate | 6.5 |
| Cream of tartar | 6.0 |
| Fragrance | 0.5 |
| Sugar | 75.0 |
| TOTAL | 100 |

The sodium bicarbonate, sodium laureth sulfate and cream of tartar were mixed together, followed by addition of the sugar and the fragrance. The mixture was then pressed into a mould and allowed to solidify to the solid exfoliating composition. The resulting solid exfoliating composition was then turned out from the mould.

The solid exfoliating composition was then massaged against the moist surface of the user's skin. This resulted in an exfoliating action which, along with the foaming action of the surfactant, removed dead skin and dirt from the skin.

Alternative formulations are made by substituting the sugar with any suitable cosmetically acceptable granular exfoliant. It will be appreciated that the choice of the granular exfoliant may well depend on the desired end application of the solid exfoliating composition. For example, where the solid exfoliating composition is intended to be used as a facial scrub, a granular exfoliant with a less abrasive nature may be selected. Alternatively, where, for example, the solid exfoliating composition is intended to be used as a foot scrub, a granular exfoliant with a more abrasive nature may be selected.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A solid exfoliating composition comprising a surfactant in an amount from about 1% to about 10% by weight of the total composition, sodium bicarbonate in an amount of from about 9% to about 18% by weight of the total composition, cream of tartar in an amount of from about 4.5% to about 9% by weight of the total composition, and a granular exfoliant in an amount of from about 50% to about 85% by weight of the total composition; wherein the solid exfoliating composition is capable of sustaining its physical shape when unsupported by an external support, wherein the sufactant selected from the group consisting of sodium laureth sulfate, cocamide diethanolamine, lauryl betaine and mixtures thereof.

2. A solid exfoliating composition according to claim 1, comprising a surfactant in an amount of from about 2% to about 8% by weight of the total composition.

3. A solid exfoliating composition according to claim 1, comprising a surfactant in an amount of from about 4.5% to about 7% by weight of the total composition.

4. A solid exfoliating composition according to claim 1, wherein the granular exfoliant is selected from the group consisting of cosmetically acceptable sugar, salt, sand, clay, seeds, ground shell, pumice and mixtures thereof.

5. A solid exfoliating composition according to claim 4, wherein the granular exfoliant is cosmetically acceptable sugar.

6. A solid exfoliating composition according to claim 5, wherein the granular exfoliant is cosmetic grade caster sugar.

7. A solid exfoliating composition according to claim 1, comprising a surfactant in an amount of about 6.5%, sodium bicarbonate in an amount of about 12%, cream of tartar in an amount of about 6%, and a granular exfoliant in an amount of about 75% by weight of the total composition.

8. A solid exfoliating composition according to claim 1, further comprising one or more cosmetically acceptable additives selected from the group consisting of essential oils, vitamins, fragrances, colourings, decorative articles and mixtures thereof.

9. A solid exfoliating composition according to claim 1, further comprising one or more cosmetically acceptable additives in an amount of from about 0.2% to about 3% by weight of the total composition.

10. A process for the production of a solid exfoliating composition as defined in claim 1 comprising the steps of:
   i) preparing a mixture comprising a surfactant, sodium bicarbonate and cream of tartar;
   ii) combining a granular exfoliant with the mixture of step i); and,
   iii) allowing the mixture of step ii) to solidify.

11. A process according to claim 10, wherein the mixture of step ii) is caused to solidify in a predetermined shape.

12. A process according to claim 10, further comprising the step of combining with the mixture of step i) or step ii) one or more cosmetically acceptable additives as selected from the group consisting of essential oils, vitamins, fragrances, colourings, decorative articles and mixtures thereof.

13. A product obtained or obtainable by the process of claim 10.

14. A cosmetic method of exfoliating the skin comprising exfoliating a skin of a user by massaging the moist skin of the user with the solid exfoliating composition as defined in claim 1.

15. A solid exfoliating composition of claim 1, wherein the granular exfoliant is selected from the group consisting of cosmetically acceptable salt, sand, clay, seeds, ground shell, pumice and mixtures thereof.

* * * * *